United States Patent [19]

Young

[11] 3,957,592

[45] May 18, 1976

[54] MEASUREMENT OF POLAROGRAPHIC CURRENT

[75] Inventor: Chung-Chang Young, Toledo, Ohio

[73] Assignee: Owens-Illinois, Inc., Toledo, Ohio

[22] Filed: July 29, 1974

[21] Appl. No.: 492,706

[52] U.S. Cl. ............................ 324/29; 204/195 B; 204/195 R
[51] Int. Cl.² ........................................ G01N 27/46
[58] Field of Search ............ 204/1 T, 195 B, 195 P, 204/195 R, 1 E

[56] References Cited
UNITED STATES PATENTS

| | | | |
|---|---|---|---|
| 3,421,982 | 1/1969 | Schultz et al. | 204/195 B |
| 3,539,455 | 11/1970 | Clark | 204/1 T |
| 3,542,662 | 11/1970 | Hicks et al. | 204/195 P |
| 3,857,771 | 12/1974 | Sternberg | 204/195 B |

OTHER PUBLICATIONS

Malmstadt et al., "J. of Chemical Education," Vol. 43, No. 7, July, 1966, pp. 340–353.

*Primary Examiner*—T. Tung
*Attorney, Agent, or Firm*—Steve M. McLary; Edward J. Holler

[57] ABSTRACT

Apparatus and method for the measurement of a cell current. A polarographic cell, which may be a two or three electrode system, furnishes a cell current which is a measure of a particular constituent of a material under test in the cell. The electrodes are continuously washed by a buffer solution which gives a base line or steady state current. The current from the cell is converted to a voltage for ease of measurement. The first derivative with respect to time is taken of the voltage. When this rate of change of voltage exceeds a preselected level, a signal is generated. This signal causes a sample and hold unit to hold and present as a constant output the voltage level at that time. This is the steady state value. The signal also resets a peak detector which accepts the cell voltage and tracks its value until a maximum is reached. Then, the maximum value is held as a constant output quantity. An electronic difference amplifier subtracts the steady state voltage from the maximum detected voltage to give a value of voltage representing the true peak level.

12 Claims, 3 Drawing Figures

MEASUREMENT OF POLAROGRAPHIC CURRENT

BACKGROUND OF THE INVENTION

This invention generally relates to polarographic cells which furnish a cell current. More specifically, this invention relates to such cells in which the electrodes are constantly washed by a buffer solution. Most particularly, this invention relates to an improved method and apparatus for measuring the cell current.

Plural electrode type polarographic measurement cells are known in the art. For example, such cells can be used to determine glucose content in human blood samples. The glucose content is determined by converting glucose to gluconic acid and hydrogen peroxide by reaction by an enzyme such as glucose oxidose in the presence of oxygen. Then, the hydrogen peroxide may be polarographically oxidized and the resulting current measured as being proportional to the glucose content of the sample under test.

An improved system in which the electrodes are continuously washed with a buffer solution is the subject of a co-pending U.S. Patent application. The continuous buffer wash generates a steady state current whose value may vary somewhat with time. In addition, this value must be subtracted from any peak current measured in order to obtain a true reading for the glucose concentration in any test sample. Furthermore, it would be highly desirable to make the measurement system as automatic as possible so that all an operator of the system need do is inject a sample and later read the peak current value. I have developed a measurement system which will sense the injection of a sample, hold the value of the steady state current at that time, sense the reaching of the peak current value, and subtract the steady state value from the peak value to give a true measure of the peak value. The system will give notice when a sample run is completed, and will reset itself each time a new sample is injected to allow rapid multiple sample testing. All an operator need do is inject the sample and read the peak values.

SUMMARY OF THE INVENTION

My invention is an improvement in the measurement of the cell current generated by a polarographic cell. In this cell, the electrodes are continuously washed by a buffer solution. An electrical current is generated by the oxidation of hydrogen peroxide carried by the buffer solution past the electrodes. The current is first converted to an equivalent cell voltage. A control means generates a first signal when the cell voltage is below a pre-selected rate of change and a second signal when the cell voltage is greater than the pre-selected rate of change. An electronic means holds and passes as a constant voltage signal a voltage equal in magnitude to the value of the cell voltage at the time of generation of the second signal. A peak detector means holds and passes as a constant value the maximum value reached by the cell voltage. A subtraction means electronically subtracts the voltage signal equal in magnitude to the value of the cell voltage at the time the second signal is generated from the voltage signal representing the maximum value reached by the cell voltage and furnishes a voltage signal equal to the difference thereof.

DETAILED DESCRIPTION OF THE DRAWINGS

Figure 1:
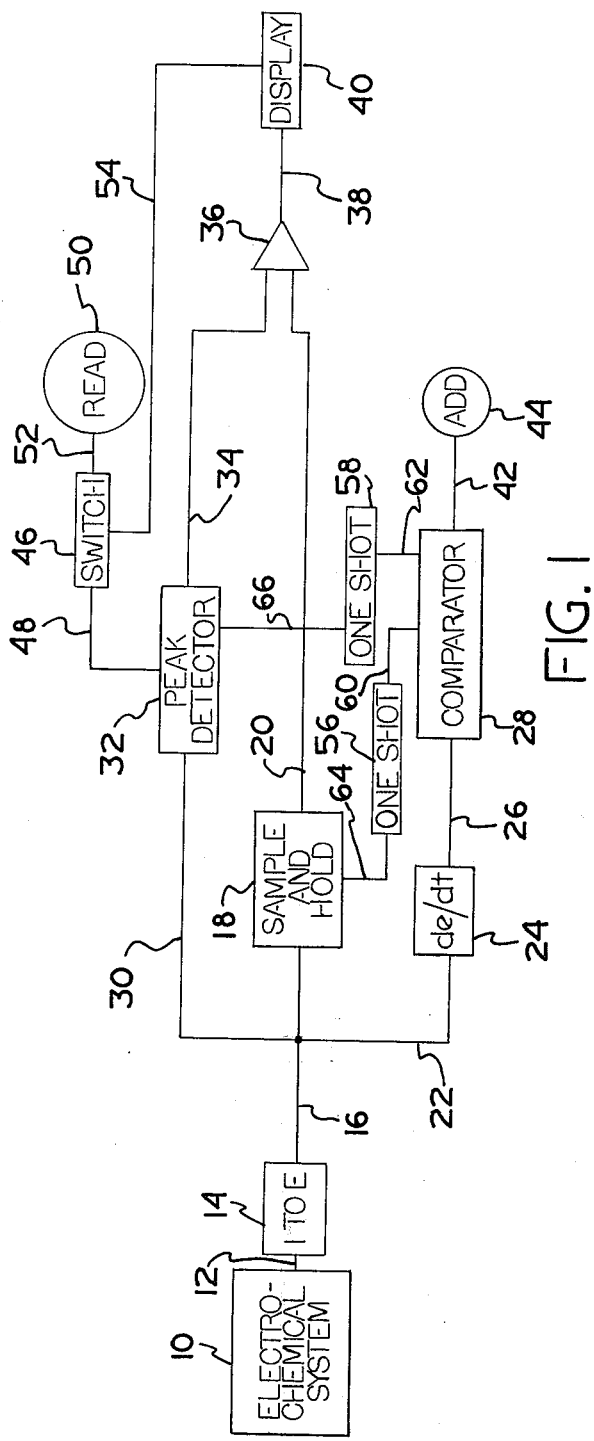
FIG. 1 is a block diagram of the present invention.

In FIG. 1, an electro-chemical system 10 furnishes an output or cell current signal on an output conductor 12. The cell current is a current which is generated in response to the oxidation of hydrogen peroxide in a polarographic cell. The generation of hydrogen peroxide from various bio-chemical solutions and its subsequent oxidization to determine concentrations of constituents within the solution is a technique well known in the art. Measurement of the current so generated thus allows the determination of the concentration of particular elements in the biological sample under study. An example of a specific type of electro-chemical system 10 with which the present invention may be used may be seen in co-pending U.S. Pat. application Ser. No. 477,922, filed June 10, 1974, having an assignee in common with the assignee of the present invention. The teachings of this co-pending patent application are hereby incorporated by reference. The conductor 12 is connected to an $i$ to $e$ converter 14. The $i$ to $e$ converter converts the current signal from the electro-chemical system 10 into a voltage signal or cell signal voltage which is more readily useable by commercial electronic components. The signal from the $i$ to $e$ converter 14 is transmitted along a conductor 16 to a sample and hold unit 18. The sample and hold unit 18 is designed to hold and present as a constant output value a base line value of the current furnished by the electro-chemical system 10.

Figure 2:
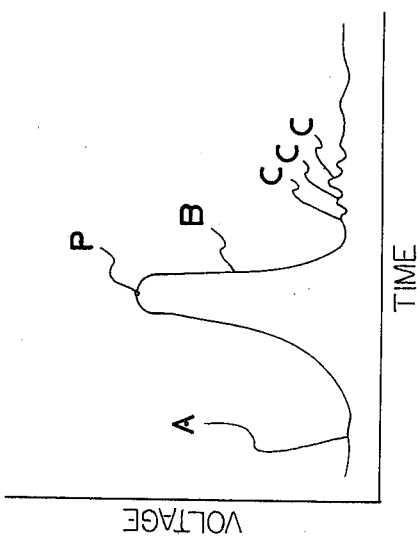
FIG. 2 is a time versus voltage waveform illustrating a typical sample run.

With reference to FIG. 2, it may be seen that the signal generated by the electro-chemical system 10 has a basically steady state component generally designated as A. When the oxidation of hydrogen peroxide begins, a rather sharply defined waveform designated as B occurs. The steady state level A is a result of the continuous operation of the system even when a sample is not being measured. While the component A is designated as being steady state, it may vary somewhat over a period of time. Thus, it is necessary that the sample and hold unit 18 interrogate the portion A of the curve each time before a measurement of the waveform B is begun. This ensures that a proper comparison of the absolute value of the peak portion P of waveform B is made with the starting level designated A. It will also be noted in FIG. 2, that the level designated as A may ripple somewhat even when samples are not being measured. These ripples are generally designated as C, and compensation for these ripples will be explained later.

Returning now to FIG. 1, to explain again, the sample and hold unit 18 will hold and furnish as an output signal on an electrical conductor 20 the value of the steady state component A which is present just as the waveform B generated by a sample begins. A branch conductor 22 connects the signal from the electro-chemical system 10 to an electronic differentiation unit 24. The differentiation unit 24 takes the first derivative with respect to time of the cell current, or more properly, since the $i$ to $e$ converter 14 is used, the cell voltage. This signal is then fed through an electrical conductor 26 to a comparator 28. In the comparator 28, the signal furnished by the differentiation unit 24 is compared with a pre-selected rate of change of the cell voltage. So long as the rate of change of the cell voltage is below this preselected level, the output of the comparator unit 28 will be a first electrical signal value. However, once this rate of change value is exceeded, the output of the comparator 28 will switch to a second, discrete electrical signal value. The initial rise of the waveform B of the curve in FIG. 2 is that level which is preset into the comparator 28. When the waveform B begins its rise, the comparator 28 will switch from its first value to its second value. The differentiation unit 24 and the comparator 28 function as a control means for electronically generating a first signal when the cell voltage is below a pre-selected rate of change and a second signal when the cell voltage is above or greater than the pre-selected rate of change. A branch conductor 30 connects the signal in the line 16 to a peak detector 32. The peak detector 32 is designed to follow the rise of the voltage signal represented by the waveform B until it reaches its maximum value generally designated as P in FIG. 2. At this point, the peak detector will hold this maximum voltage value of P and will furnish this value as an output along a conductor 34. The conductor 34 furnishing the peak value is connected to one input of a difference amplifier 36. The conductor 20, which furnishes the signal from the sample and hold unit 18 that represents the steady state value designated as A in FIG. 2, is connected to a second input of the difference amplifier 36. The output of the difference amplifier 36 carried by a conductor 38 is the difference between the value P and the value represented by A at the beginning of the rise of the waveform B. This particular function is necessary since the value A can vary somewhat over a period of time, due to fluctuations within the system, and the number which is desired for accurate measurement is the actual maximum value of current, or in this case voltage, and its level above A. Thus it is necessary to subtract the steady state component A from the actual peak reading P to give a number which is representative of the absolute maximum voltage value. The conductor 38 then carries this difference to a display unit 40 where it is displayed. The display unit 40 may be any type of conventional voltage display device such as a volt meter with a moving dial, a strip-type recorder, or, preferably, a digital volt meter. This number then given an indication of the concentration of the biological component under investigation within the solution being measured.

The operation of the system is as follows: assuming that the system has been in a steady value for a relatively long period of time and no sample has been measured, it is first necessary to ascertain the condition of each of the components within the system. The sample and hold unit 18 will be holding a value which is representative of the last steady state value A which it sampled and will be furnishing this value to the difference amplifier 36. The peak detector 32 will be holding a value which represents the last peak P which it held and will also be furnishing this value to the difference amplifier 36. The display unit 40 will be displaying the number which was representative of the last peak which was measured. The comparator 28 furnishes through a conductor 42 a signal to an add sample light 44 which is turned on when the waveform B reaches its lowermost portion. The illumination of the add sample light 44 indicates that the system is ready for a new sample to be added. The peak detector 32 also controls a switch 46, which may be a transistor switch or any other convenient device which may be electrically controlled, through a conductor 48. The switch 46 is actuated to turn on a read light 50 which is connected by a conductor 52 to the switch 46. The read light 50 is turned on when the peak detector 32 determines that peak of the waveform B has been reached. The switch 46 also controls the display unit 40 through a conductor 54 which interconnects the two units. So long as the peak detector 32 has not reached the maximum value of the waveform B, a signal is present on the conductor 54 to the display unit 40 which allows the display unit 40 to continue to change its output display. However, when the peak value P has been reached, the signal along the conductor 54 ceases and the display unit 40 will no longer change its value, but will be locked into the last number which was displayed. Thus, at this stage, even though the difference amplifier 36 is furnishing a signal to the display unit 40 the display unit 40 will not change in response to any change of the output signal of the difference amplifier 36. This particular function is optional, and is provided simply because some of the components within the peak detector 32 and the sample and hold unit 18 are not perfect. Over a long period of time, the values held therein may drift somewhat and thus if the display unit 40 were not read immediately, it could give erroneous results if read some period of time later. Therefore, the number into the display unit 40 is locked at the time that the peak P of the waveform B is reached, thus ensuring that an accurate reading of the material measured may be made a long period of time after the test is actually completed. If the display unit 40 were read immediately or if all the components within the system were ideal, the function of the switch 46 to control the display unit 40 would not be necessary. Now assume that a sample has been injected and the waveform B begins to rise from the general level designated as A. At this time, the differentiation unit 24 will begin to furnish a signal to the comparator 28 indicating that the rate of change of the voltage is beginning. When this rate of change reaches the pre-selected level, the comparator 28 will trigger two monostable multi-vibrators or one shot units 56 and 58. The one shot units are respectively connected to the comparator 28 through electrical conductors 60 and 62. The one shot 56 is connected through a conductor 64 to the sample and hold unit 18. The signal from the one shot 56 to the sample and hold unit 18 allows the sample and hold unit 18 to accept and hold the voltage signal from $i$ to $e$ converter which is present at that time. This is the steady state level A and indicates the beginning of a new waveform B. The one shot 56 furnishes a pulse of a relatively short duration so that the value is entered into the sample and hold unit 18 and then held with no further information entered in the sample and hold unit during the specimen measuring process. The one shot 56 has virtually no delay before it turns on after receiving a signal from the comparator 28. This is provided so that the sample and hold unit 18 is always quick to accept any indication that a rise in level is beginning which might indicate the commencement of a sampling process. The time the signal from the one shot 56 is on is very short, for example 20 milliseconds, so that the true value at the beginning of the measurement may be stored. Thus, the ripple waveforms designated as C will trigger the sample and hold unit 18 to accept a new value. However, it would be undesirable to begin a total measuring process because of the ripple waveform C. Thus, the one shot 58, which is connected to the peak detector 32 by a conductor 66, has a much longer time delay before it is turned on than does the one shot 56. The one shot 58 may be set so that it will not turn on until approximately one second after the signal has been received from the comparator 28. The waveform B is not an extremely rapidly moving waveform, so there is no danger of any information being lost as a result of this turn-on delay. When this delay period has expired, the peak detector 32 will be reset by a pulse from the one shot 58 along the conductor 66. This will allow the peak detector 32 to begin to accept the changing electrical signal generated by the waveform B as it rises toward its peak P. Also at this time, with the peak detector 32 now actuated, the switch 46 will be turned on, which will turn off the read light 50 and turn on the display unit 40 to allow acceptance of the signal from the difference amplifier 36. Simultaneously with the signal to the one shot units 56 and 58 from the comparator 28, the add sample light 44 will also be turned off. As the waveform B rises to a peak, the peak detector 32 will hold the peak value P. When the peak value P is reached, the switch 46 will again disable the display unit 40 to prevent changing of the value held at that time and will turn on the read light 50. As the waveform B falls, on the negative slope side of the waveform B, the comparator 28 continues to receive input information from the differentiation unit 24. At the time when the signal from the differentiation unit 24 has fallen below the level necessary to trigger the comparator 28, the add sample light 44 will be turned on again through the comparator 28. Note that the one shot units 56 and 58 will not be triggered by the falling waveform B, although the add sample light 44 will be turned on. This is precisely the condition in which the entire system is found after a long period of time has elapsed with no further samples having been added.

Figure 3:
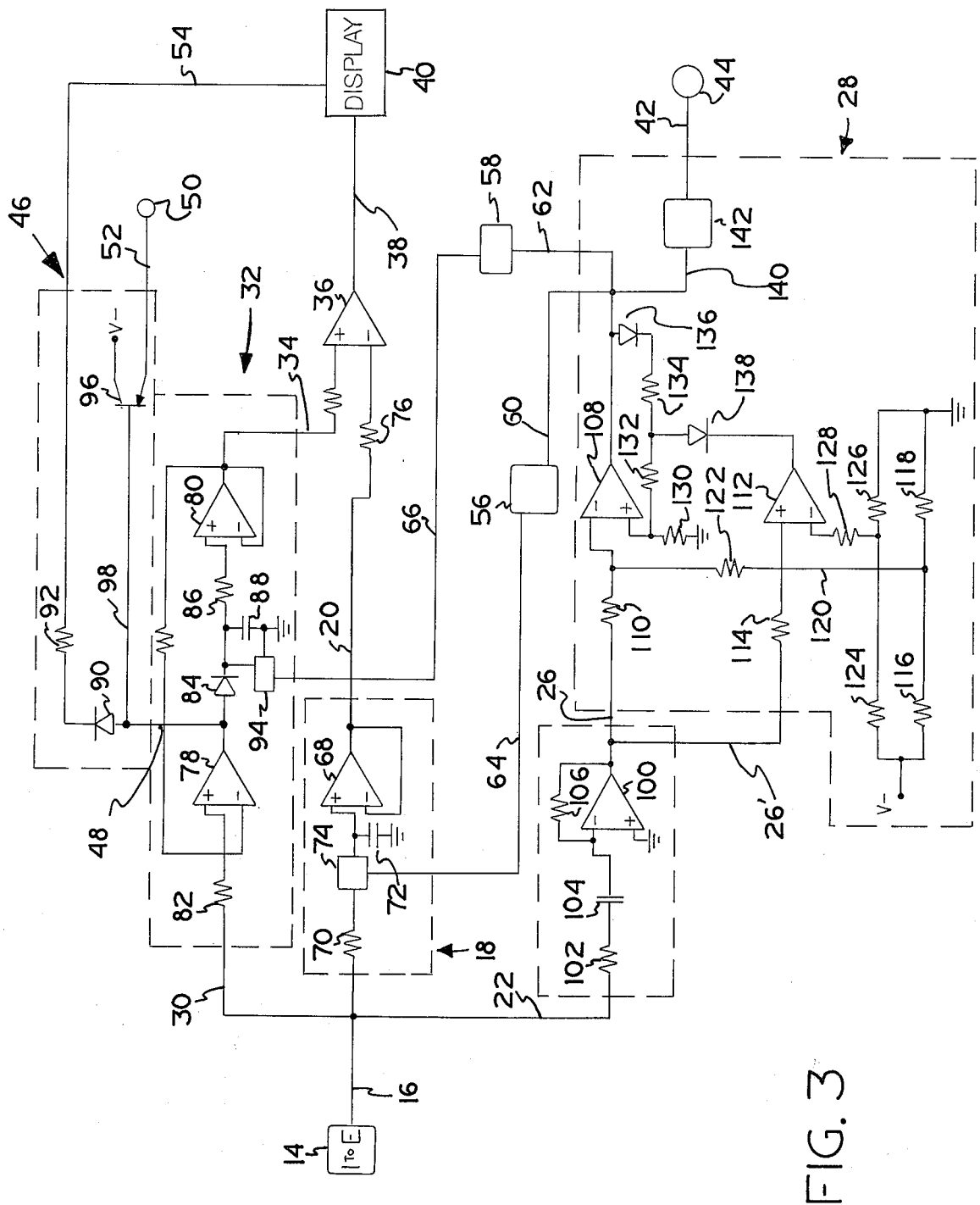
FIG. 3 is a schematic circuit diagram of the present invention.

FIG. 3, a circuit diagram of the present invention is shown. In this circuit diagram, some resistors and capacitors which are normally included for noise suppression or for signal smoothing have been omitted. However, the utilization and the placement of such elements would be obvious to those skilled in the art. In addition, it is assumed that the circuit has available a positive voltage supply and a negative voltage supply respectively designated as $v+$ and $v-$. Likewise, the use of specific voltage signs, that is positive or negative voltages, should be taken by way of example and not by way of limitation. The $i$ to $e$ converter 14 is of the conventional type well known in the art which uses an operational amplifier to provide the conversion function. The sample and hold unit 18 includes an operational amplifier 68. The operational amplifier 68 has positive and negative input terminals and an output terminal which is connected to the conductor 20. The conductor 16 is connected to the positive input terminal of the operational amplifier 68 through an input resistor 70. A capacitor 72 is connected to the conductor 16, intermediate the resistor 70 and the positive input terminal of the operational amplifier 68, and to ground. A switching means 74 is connected in series in the conductor 16 before the capacitor 72 and after the resistor 70. The purpose of the switching means 74 is to isolate the capacitor 72 from the signal furnished by the conductor 16. The operational amplifier 68 simply serves as an isolation element to avoid draining the capacitor 72 rapidly. The capacitor 72 thus may hold a charge and furnish a voltage signal for a relatively long period of time. Since the operational amplifier 68 does simply serve as an isolation element, the negative input terminal is connected to the output of the operational amplifier 68 to complete a feedback loop. Switching means 74 may be an electronic switching device such as a transistor or may be an electro-mechanical device such as a simple relay. Whatever the case, the switching means 74 is controlled by the one shot unit 56. Whenever a signal is presented by the one shot unit 56, switch 74 is turned on. This will reset the capacitor 72 since at this time the capacitor 72 will accept whatever value is presented along the conductor 16. When the pulse from the one shot unit 56 ceases, switch 74 will be turned off. This will isolate the capacitor 72 from any further signal, and it will thus hold the last value that was impressed upon it and will present this value as an output from the operational amplifier 68. As will also be apparent, the difference amplifier 36 is likewise an operational amplifier with positive and negative input terminals. The output from the operational amplifier 68 is connected to the negative input terminal of the difference amplifier 36 through a resistor 76. The peak detector 32 is a somewhat more complex element. Two operational amplifiers 78 and 80 are used in the peak detector 32. Both the operational amplifiers 78 and 80 have positive and negative input terminals and output terminals. The conductor 30 is connected to the positive input terminal of the operational amplifier 78 through a resistor 82. A diode 84 and a resistor 86 are connected in series between the output of the operational amplifier 78 and the positive input terminal of the operational amplifier 80. A capacitor 88 is connected intermediate the diode 84 and the resistor 86 and is also connected to ground. The negative input terminal of the operational amplifier 80 is tied to the output terminal of the operational amplifier 80. Thus, the operational amplifier 80 also acts as a simple isolation amplifier as did the operational amplifier 68. In this case, it is the capacitor 88 which carries a value, in this case the peak value P from the waveform B, which is presented as a steady output from the operational amplifier 80. The output terminal of the operational amplifier 80 is also connected to the negative input terminal of the operational amplifier 78. Assume that the waveform B is just beginning its rise. At this point, the capacitor 88 has no charge on it. The signal coming into the operational amplifier 78 is a positive signal which will pass through the diode 84, the resistor 86 and into the operational amplifier 80, charging the capacitor 88 in the process. Capacitor 88 will begin to charge and will assume whatever voltage level is presented by the operational amplifier 78. The output of the operational amplifier 80 will be fed into the negative input of the operational amplifier 78. As the peak P of waveform B is passed, the signal from the operational amplifier 80 will be greater than the signal furnished from the conductor 30 since the voltage value is now beginning to fall. This means that the output from the operational amplifier 78 will switch from a positive value to a negative value. The diode 84 prevents passage of a negative in sign voltage signal. Thus, the capacitor 88 will retain the highest voltage level that has been passed. Also note that the conductor 48 is connected to the output of the operational amplifier 78. A diode 90 is connected in series with a resistor 92 to the conductor 54 connected to the display unit 40. So long as the positive voltage is furnished by the operational amplifier 78, a current will flow through the diode 90 and the resistor 92 to the display unit 40. The display unit 40 may be a digital voltmeter which requires a voltage to be present at its input terminal before it will accept a value for display. Thus, so long as this value is present the display unit 40 will accept and register values furnished to it from the difference amplifier 36. However, after the peak P of the waveform B has been passed, the voltage that is furnished to the diode 90 will be negative in sign and no further voltage will be furnished to the display unit 40. Thus the display unit 40 will accept no further signals from the difference amplifier 36 but rather will be locked into displaying its last value prior to the cessation of the signal furnished by the conductor 54. The signal on the conductor 54 will cease, as previously pointed out, at the point at which the peak P of the waveform B has been reached. The capacitor 88 is reset under the control of a switching means 94 which is connected intermediate the diode 84 and the capacitor 88 and is connected to ground. The switching means 94 may be an electronic switch such as a transistor or an electro-mechanical switching device such as a relay. In either case, the one shot unit 58 will furnish a pulse along the conductor 66 connected to the switching means 94 for turning the switching means 94 on. So long as the pulse is present from the one shot unit 58, switching means 94 will be on. When this pulse is not present, the switching means 94 will be off. When the switching means 94 is off, the capacitor 88 has only one plate connected to ground and thus may hold the voltage presented to it. However, when the switching means 94 is turned on, both plates of the capacitor 88 are connected to ground, the plate normally not connected to ground being so connected by the switching means 94 at this time, and the capacitor 88 is thus discharged to a zero value. This discharging or resetting of the capacitor 88 takes place at the time a waveform B begins to rise from the normal level A. Remember again, that the one shots 56 and 58 have very different time delays before they are turned on so that the peak detector 32 does not have its capacitor 88 reset by small rippling waveforms such as C. One final point is that within the switch 46 is also contained a transistor 96. The transistor 96 is of the type which is normally off so long as a positive signal is present at the base. A conductor 98 connects the base of the transistor 96 to the conductor 48 carrying the signal from the operational amplifier 78. The collector of the transistor 96 is connected to the v-supply and the emitter of the transistor 96 is connected to the conductor 52 which is connected to the read light 50. So long as the value of the voltage on the conductor 48 is positive, the transistor 96 is off and the read light is also off because of the transistor 96 being off. However, when the voltage becomes negative, the transistor 96 will be turned on which in turn will turn on the read light 50, thus indicating that a peak P has been reached and the value on the display unit 40 should be read to obtain this number.

The major component of the differentiation unit 24 is an operational amplifier 100 which has positive and negative input terminals and an output terminal. The operational amplifier 100 has the positive input terminal grounded. A resistor 102 and a capacitor 104 are connected in series to the negative input terminal of the operational amplifier 100 and to the conductor 22 from the i to e converter 14. The positioning of the capacitor 104 on the input side of the operational amplifier causes the operational amplifier 100 to operate as a differentiating unit as is well known in the art. Thus the output of the operational amplifier 100 is the first derivative with respect to the time of the input signal from the electro-chemical system 10. A feedback loop is formed through a resistor 106 connecting the negative input terminal and the output terminal of the operational amplifier 100. It is important to realize at this point that the output signal from the operational amplifier 100 will be inverted in voltage sign with respect to the input signal. This results because of the connection of the input signal to the negative or inverting terminal of the operational amplifier 100. Thus the value of the output of the operational amplifier 100 will be negative in voltage sign as the slope of the waveform B is rising and positive in sign as the slope of the waveform B is falling.

The conductor 26 connects the differentiation unit 24 to the negative input terminal of an operational amplifier 108 of the comparator unit 28 through an input resistor 110. A branch conductor 26' connected to the conductor 26 is connected to the positive input terminal of an operational amplifier 112 through an input resistor 114. The operational amplifiers 108 and 112 make up the primary elements of the comparator unit 28. Two resistors 116 and 118 are connected in series to the negative voltage supply and to ground. The resistors 116 and 118 form a voltage divider for furnishing a biasing voltage to the operational amplifier 108 through a conductor 120 with a resistor 122 connected in series in the conductor 120. The conductor 120 is connected intermediate the input resistor 110 and the negative input terminal of the operational amplifier 108. A second pair of series-connected resistors 124 and 126 are also connected to the negative voltage supply and to ground and serve to form a voltage divider for furnishing a biasing voltage to the operational amplifier 112. These biasing voltages define the preselected rate of change the cell voltage must attain before a measurement will be made. This voltage is furnished through a resistor 128 connected between the resistors 124 and 126 and to the negative input terminal of the operational amplifier 112. The positive input terminal of the operational amplifier 108 is connected to ground through a resistor 130. Two additional resistors 132 and 134 are connected in series with a diode 136 in a feedback loop between the output of the operational amplifier 108 and the positive input terminal of the operational amplifier 108. The output of the operational amplifier 112 is connected intermediate the resistors 132 and 134 through a diode 138. The diodes 136 and 138 are biased such that they will not permit passage of voltage signals from operational amplifier 112 which are positive in sign but will pass voltage signals which are negative in sign. As was noted earlier, the output of the operational amplifier 108 is connected to the one shot units 56 and 58 through the conductor 60 and 62. A conductor 140 also connects the output of the operational amplifier 108 to a switching means 142 which controls the operation of the add sample light 44 through the conductor 42 connected to the switching means 142. The switching means 142 is preferably a device which is sensitive to the sign of the voltage signal presented to it, such as a transistor. The switching means 142 is thus biased so that it will normally be off so long as a sample is being measured and will be on after the sample has been completely measured. In this case, the add sample light 44 will also be on so long as the switch 142 is also on. The operational amplifiers 108 and 112 are constrained to act as comparator units and will give one of two discrete outputs, for example −12 volts or +12 volts, depending upon whether or not the input signal received is greater than or less than a biasing signal presented to them. Consider first the situation which prevails when the system is at rest a long period of time after a sample has been added. Under these conditions, the system is ready for a sample to be added and a new measurement to be made. At this time, the output of the differentiation unit 24 will be essentially zero since there is no appreciable change in the voltage level at this time. With a zero input to the operational amplifier 108 through the resistor 110, the only input to the operational amplifier 108 is through the voltage divider and resistor 122 which furnishes a negative voltage to the negative input terminal. This then means that the output of the operational amplifier 108 will be positive in sign, the +12 volt signal, since the only other input to the operational amplifier 108 is through the grounded resistor 130. When the output along the conductor 140 is positive in sign the switching means 142 is on and the add sample light 44 is also on. Also under these conditions, the operational amplifier 112 is receiving a zero input to its positive input terminal through the resistor 114. The only input then is through the negative input terminal which is furnished a negative in sign voltage signal through the resistor 128. This means that the output of the operational amplifier 112 is also positive in sign. The diode 138 blocks propagation of this particular output signal level any further than the diode 138. When a sample is added, generation of waveform B begins. As waveform B begins, the output of the differentiation unit 24 will show a varying value indicating that the slope of the signal is changing. Keep in mind that this value will be negative in sign for a rising slope. The connection of the resistors 122 and 110 means that the input to the negative input terminal of the operational amplifier 108 is the sum of the voltages furnished to that point. Thus with a negative input signal being furnished through the resistor 110, and a negative biasing signal furnished to the resistor 122, the output of the operational amplifier 108 will remain positive since the net input thereto is still negative in sign. However, note that the resistor 114 is now furnishing a signal which is negative in sign to the positive input terminal of the operational amplifier 112. When this value becomes greater than the biasing voltage furnished through the resistor 128 to the negative input terminal of the operational amplifier 112, the output of the operational amplifier 112 will switch from the positive in sign voltage to a negative in sign voltage. When the output of the operational amplifier 112 switches from the positive to the negative voltage level, the diode 138 will allow this signal to be propagated through the resistors 132 and 130. This will then furnish a negative in sign signal to the positive input terminal of the operational amplifier 108. This voltage value is such that it will be greater than the input value from the resistors 110 and 122. This will then switch the output of the operational amplifier 108 from a positive in sign signal to a negative in sign signal. The one shot units 56 and 58 are constructed such that they will be triggered to generate their output pulse only upon the transition of their input signals from a positive in sign signal to a negative in sign signal. Therefore, these units will reset the peak detector 32 and the sample and hold unit 18 at this time. Also note that since the value is now negative in sign the switching means 142 will be turned off since it is on only when a positive in sign signal is furnished to it. This will also turn off the add sample light 44 indicating that a test is in process. So long as the slope of the waveform B is rising, the input to the operational amplifier 112 will remain negative in sign and the circuit will remain in the condition just described. However, when the peak of the waveform B is reached the output of the differentiation unit 24 will immediately switch from a relatively high signal value that is negative in sign to substantially the same value which is positive in sign and will then decay down to the normal level. When this occurs, the input to the operational amplifier 112 through the resistor 114 is now positive in sign. This value is greater than the negative in sign biasing voltage furnished through the resistor 128 and the output of the operational amplifier 112 thus switches from the negative output level to the positive output level. This then in turn switches off the diode 138 or more properly prevents propagation of the signal beyond the diode 138 and thus removes the voltage previously furnished the positive input terminal of the operational amplifier 108. However, note that at this point the input to the operational amplifier 108 is through the resistor 110 which now has furnished to it a relatively large in magnitude positive in sign signal and through the resistor 122 which has a much smaller but negative in sign biasing signal. Thus the signal furnished through the resistor 110 predominates at the input to the negative input terminal of the operational amplifier 108 and is positive in sign. The output of the operational amplifier 108 thus remains negative in sign. As the waveform B decays, the voltage signal furnished through the resistor 110 becomes smaller and smaller until eventually the negative biasing voltage furnished through the resistor 122 predominates. At this point the input to the negative input terminal of the operational amplifier 108 will once again be negative in sign. When this occurs, the output of the operational amplifier 108 will switch from the negative level to the positive level. This occurs at the very base of the waveform B on the falling side thereof. This is the normal stable system level. When this transition occurs, the switching means 142 will be turned on which will illuminate the add sample light 44 indicating that the test is completed and a new sample can be added. Also note that at this point the transition is from a negative in sign voltage to a positive in sign voltage. This transition will not trigger the one shot units 56 and 58 since they are triggered only upon transition from a positive in sign voltage to a negative in sign voltage. Thus the sample and hold unit and peak detector units will not be reset at this point, but rather will be reset only upon the occurrence of the measurement of a new sample.

I claim:

1. In a polarographic cell of the type wherein the electrodes are continuously washed by a buffer solution, and wherein an electrical cell current is generated by the oxidation of hydrogen peroxide carried by the buffer solution past said electrodes, the improvement in measuring said cell current which comprises:
   means for converting said cell current to an equivalent cell signal voltage;
   control means, connected to said cell signal voltage, for electronically generating a first signal when said cell signal voltage is below a pre-selected rate of change and a second signal when said cell signal voltage is above said pre-selected rate of change;

means, connected to said cell signal voltage and said control means, for electronically holding and passing a constant voltage signal, equal in magnitude to the value of said cell signal voltage at the time said second signal is generated, in response to said second signal;

peak detector means, connected to said cell signal voltage and said control means, for holding and passing as a constant voltage signal the maximum value reached by said cell signal voltage, said peak detector means being responsive to said second signal to release any previous peak value held therein; and subtraction means for electronically subtracting said voltage signal equal in magnitude to the value of said cell signal voltage at the time said second signal is generated from said voltage signal representing the maximum value reached by said cell signal voltage and furnishing a voltage signal equal to the difference thereof.

2. The improvement of claim 1 which further includes:

means, connected to said subtraction means, for displaying the value of the output signal of said subtraction means.

3. The improvement of claim 1 which further includes:

a signal light; and switch means, connected to said peak detector means and said signal light, for turning said signal light on and off, said switch means being responsive to the reaching of said maximum value and turning on said signal light in response to reaching said maximum value.

4. The improvement of claim 3 which further includes:

means, connected to said subtraction means and said switch means, for displaying the value of the output signal of said subtraction means and responsive to said switch means to accept an input from said subtraction means only until said maximum value is reached.

5. The improvement of claim 1 which further includes:

a signal light connected to said control means, said signal light being on when said first signal is present and off when said second signal is present.

6. The apparatus of claim 1 which further includes:

a monostable multivibrator, connected to said control means and said means for electronically holding and passing a constant voltage signal, responsive only to the transition from said first signal to said second signal to generate a pulse to cause said means for electronically holding and passing a constant voltage signal to release a previously held voltage value and accept and hold the voltage value present at the time of generation of said pulse.

7. The apparatus of claim 1 which further includes:

a monostable multivibrator, connected to said control means and said peak detector means, responsive only to the transition from said first signal to said second signal to generate a pulse to cause said peak detector means to release a previously held maximum value and accept new voltage values until a new maximum value is reached.

8. The apparatus of claim 1 wherein said control means includes:

means, connected to said signal voltage, for electronically generating a signal quantity equivalent to the first derivative with respect to time of said signal voltage; and comparator means, connected to said derivative signal quantity, for comparing said signal quantity with a pre-selected signal level and for generating a first signal if said derivative signal quantity is less than said pre-selected level and a second signal if said derivative signal quantity is greater than said pre-selected level.

9. In a method of measuring biological fluids wherein a polarographic cell is continuously washed by a buffer solution and wherein an electrical cell current is generated by the oxidation of hydrogen peroxide carried by the buffer solution past the cell electrodes, an improved method of measuring said cell current which comprises the steps of:

electronically converting said cell current to an equivalent cell signal voltage;

electronically generating a signal quantity representing the time rate of change of said cell signal voltage;

electronically generating a first signal when said time rate of change is less than a pre-selected value;

electronically generating a second signal when said time rate of change is greater than said pre-selected value;

electronically holding and passing as a constant voltage signal the value of said cell signal voltage present at the time of generation of said second signal;

electronically measuring and holding the maximum value reached by said cell signal voltage; and electronically subtracting said constant voltage signal from said maximum value of said cell signal voltage to thereby generate a difference voltage.

10. The improved method of claim 9 which includes the further step of:

displaying as a visual output said difference voltage.

11. The improved method of claim 9 which includes the further step of:

illuminating a signal light in response to said cell signal voltage reaching said maximum value.

12. The improved method of claim 9 which includes the further step of:

illuminating a signal light when said time rate of change of said cell signal voltage falls below said pre-selected value after said cell signal voltage has reached a maximum value.

* * * * *